(12) United States Patent
Ross

(10) Patent No.: US 6,184,411 B1
(45) Date of Patent: Feb. 6, 2001

(54) PROCESS FOR THE PREPARATION OF SUBSTITUTED HYDROXYHYDROCINNAMATE ESTERS BY REMOVAL OF TIN CATALYSTS

(75) Inventor: John Richard Ross, Mobile, AL (US)

(73) Assignee: Ciba Specialty Chemicals Corporation, Tarrytown, NY (US)

( * ) Notice: Under 35 U.S.C. 154(b), the term of this patent shall be extended for 0 days.

(21) Appl. No.: 09/238,564

(22) Filed: Jan. 28, 1999

Related U.S. Application Data

(60) Provisional application No. 60/073,402, filed on Feb. 2, 1998.

(51) Int. Cl.[7] .................. C07C 69/88; C07C 69/76
(52) U.S. Cl. .................. 560/67; 560/55; 560/75; 560/87; 560/89; 560/95
(58) Field of Search .................. 560/67, 75, 87, 560/89, 95, 55

(56) References Cited

U.S. PATENT DOCUMENTS

| 4,594,444 | 6/1986 | Orban ........................ 560/67 |
| 5,481,023 | 1/1996 | Kleiner et al. ................ 560/75 |

FOREIGN PATENT DOCUMENTS

| 0300055 | 1/1989 | (EP) . |
| 0448775 | 10/1991 | (EP) . |
| 1316389 | 12/1989 | (JP) . |

Primary Examiner—James O. Wilson
Assistant Examiner—Robert W. Deemie
(74) Attorney, Agent, or Firm—Luther A. R. Hall; Michele A. Kovaleski

(57) ABSTRACT

The invention is directed to an improved process for the preparation of a compound of formula (I)

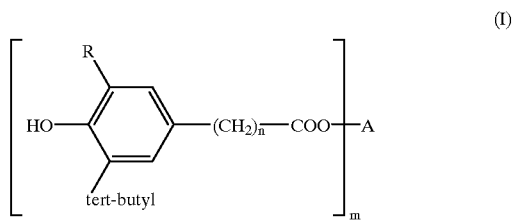

wherein R is alkyl, n is 0 to 2, m is 1 to 4 and A is alkyl, interrupted or uninterrupted alkylene, alkanetriyl or pentaerythrityl, by transesterifying the corresponding lower alkyl with a higher alkanol of the formula $A\text{-}(OH)_m$ in the presence of a tin catalyst; wherein the improvement comprises reacting the tin catalyzed transesterification reaction mass with a carboxylic acid or hydrate thereof neat, in the absence of an aqueous medium, until the tin catalyst forms an insoluble derivative, and then separating the insoluble derivative from the reaction mass by filtration without the assistance of a filtration aid. The invention allows for a convenient method by which to remove the residual tin catalyst from the substituted hydroxyphenylcarboxylic acid ester compounds of formula (I).

22 Claims, No Drawings

PROCESS FOR THE PREPARATION OF SUBSTITUTED HYDROXYHYDROCINNAMATE ESTERS BY REMOVAL OF TIN CATALYSTS

This application claims the benefit under 35 USC 119(e) of U.S. Provisional Application No. 60/073,402, filed Feb. 2, 1998.

This invention pertains to an improved process for the removal of residual tin catalyst from substituted higher aliphatic esters of hydroxyhydrocinnamic acids made by the tin catalyzed transesterification reaction between the corresponding lower alkyl ester and higher alkanol.

BACKGROUND OF THE INVENTION

The aliphatic esters and polyesters of substituted sterically hindered hydroxy-hydrocinnamic acid are well-known as effective antioxidants for a wide variety of organic materials protecting them from oxidative and thermal degradation. Many of these esters have gained wide commercial acceptance as phenolic antioxidants.

An important known class of transesterification catalysts which may be used to prepare the above compounds include tin catalysts, particularly organotin catalysts. For example, U.S. Pat. No. 4,594,444 teaches a process for the preparation of sterically hindered hydroxyphenylcarboxylic acid esters by the transesterification of the corresponding methyl or ethyl ester with a higher aliphatic alcohol using an oxide or an organometallic compound of a metal of the fourth main group or subgroup of the periodic table as catalyst in an amount between 0.05 and 1.0 mol percent based on the methyl or ethyl ester. Higher dialkyltin oxides, particularly dibutyltin oxides, are taught as the preferred catalysts for this process.

However, as recognized in the art of antioxidants, if the amount of tin residue in the product is too high, the ultimate product stability may be compromised. Care is therefore taken to remove such residues. Unfortunately, one or more of the following disadvantages are commonly associated with known methods for removing tin residue from substituted hydroxyphenylcarboxylic acid esters: product degradation and/or color formation; additional processing steps (including, for example, crystallization or adsorption techniques) which inevitably result in yield loss and increased waste generation; and increased expense due to the need for rather sophisticated equipment which may be required for the separation of product from residual tin catalyst.

Japanese Hei 01 316389 (Takee et al.) provides for the removal of organotin compounds from general ester exchange reactions by making the organotin compounds insoluble in organic media with the use of aqueous carboxylic acid solutions. In particular, the Japanese reference requires the use of an organic solvent to make the carboxylic acid derivative of the tin compound insoluble in the ester mixture, which technique increases equipment requirements as well as waste generation. The Japanese reference further requires use of an aqueous solution of a carboxylic acid. Unfortunately, the presence of a large amount of water leads to the formation of the undesirable toxic by-product, 3-(3, 5-di-tert-butyl4-hydroxy)hydrocinnamic acid (HCA), the presence of which becomes problematic for the instant hydrohydroxycinnamate esters when employed in food contact applications. The reference further teaches the added step of using auxiliary filter aids, such as cellulose or activated charcoal, which are needed in order to effectively remove the reacted tine compound.

Clearly, need continues to exist in the industry for a simplified and improved process of removing residual tin from the substituted higher aliphatic esters of hydrohydroxycinnamic acids made by the tin catalyzed transesterification reaction between the corresponding lower alkyl ester and higher alkanol. It is the object of the present invention to satisfy this need.

BRIEF SUMMARY OF THE INVENTION

The invention is directed to an improved process for the preparation of substituted higher aliphatic esters of hydroxyhydrocinnamic acids by transesterifying the corresponding lower alkyl ester with a higher alkanol of the formula A-(OH)$_m$ in the presence of a tin catalyst. In particular, the invention provides for an improved method to remove the residual tin by reacting the tin catalyzed transesterification reaction mass with a carboxylic acid or hydrate thereof neat, in the absence of an aqueous medium, until the tin catalyst forms an insoluble derivative, and then separating the insoluble derivative from the reaction by filtration without the assistance of a filtration aid.

DETAILED DESCRIPTION

The invention is directed to an improved process for the preparation of a compound of formula (I)

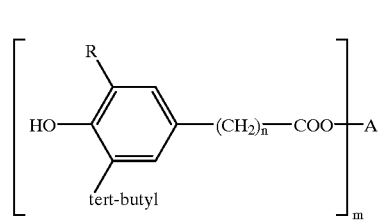

(I)

wherein R is an alkyl of 1 to 4 carbon atoms, n is 0 to 2, m is 1 to 4; and when m is 1, A is a straight or branched chain alkyl of 4 to 18 carbon atoms;

when m is 2, A is a straight or branched chain alkylene of 2 to 12 carbon atoms, or said alkylene interrupted by one to five O or S atoms, or A is 2,2-bis(4-ethyleneoxyphenyl) propane;

when m is 3, A is a straight or branched chain alkanetriyl of 3 to 6 carbon atoms; and when m is 4, A is pentaerythrityl, by transesterifying the corresponding lower alkyl ester with a higher alkanol of the formula A-(OH)$_m$                  (II)

in the presence of a tin catalyst;
wherein the improvement comprises reacting the tin catalyzed transesterification reaction mass with a carboxylic acid or hydrate thereof neat, in the absence of an aqueous medium, until the tin catalyst forms an insoluble derivative, and separating the insoluble derivative from the reaction mass by filtration without the assistance of a filtration aid.

Preferably, the lower alkyl ester is a compound of formula (I) where m is 1 and A is methyl or ethyl, most preferably methyl.

Preferably, R is methyl or tert-butyl.

When m is 1, A is preferably alkyl of 8 to 18 carbon atoms; most preferably isooctyl, lauryl or n ocladecyl; especially nectadecyl.

When m is 2, A is preferably hexamethylene, —CH$_2$CH$_2$SCH$_2$CH$_2$—or
—CH$_2$CH$_2$OCH$_2$CH$_2$OCH$_2$CH$_2$—.

When m is 3, A is preferably $CH_3C(CH_2-)_3$, $CH_3CH_2C(CH_2-)_3$ or glyceryl.

Both organic and inorganic tin catalysts may be employed in the transesterification reaction and removed according to the instant invention. Representative tin catalyst classes include monoalkyltin esters, dialkyltin esters, monoalkyltin oxides, dialkyltin oxides, tin tetrachlorides, monoalkyltin trichloride, dialkyltin dichloride, diaryltin dichlorides, organotin sulfides, organotin sulfates, organotin mercaptans, organotin carboxylic acid or esters thereof, and stannoxanes.

Preferred tin catalysts include monobutyltin tris(2-ethylhexoate), dibutyltin bis(2-ethylhexoate), stannous bis(2-ethylhexoate), dibutyltin diacetate, dibutyltin oxide, butyltin trichloride, butyltin trimethylate, dibutyltin dichloride, and diphenyltin dichloride. In particular, FASCAT® 4215A organotin catalyst, of proprietary structure belonging to the stannoxane family and containing 18.5–20.5% tin is preferred. FASCAT® 4215A organotin catalyst is available in an aromatic hydrocarbon solution from Elf Atochem, headquartered in Philadelphia, Pa. Other particularly preferred catalysts are monobutyltin tris(2-ethylhexoate) and stannous bis(2-ethylhexoate), both available from Elf Atochem under the names FASCAT™ 9102/4102 and FASCAT™ 2003, respectively.

The transesterification reaction may be one which is known in the literature. For example, U.S. Pat. No. 4,594,444 teaches a process for the preparation of sterically hindered hydroxyphenylcarboxylic acid esters by the transesterification of the corresponding methyl or ethyl ester with a higher aliphatic alcohol using an oxide or an organometallic compound of a metal of the fourth main group or subgroup of the periodic table as catalyst in an amount between 0.05 and 1.0 mol percent based on the methyl or ethyl ester. Higher dialkyltin oxides, particularly dibutyltin oxides, are taught as the preferred catalyst for this process.

The instant process has been found to be particularly effective under conditions where the transesterification reaction proceeds neat in the absence of solvent and where the amount of tin catalyst is minimized, i.e., on the order of about 50 to about 120 ppm tin, based on the starting lower alkyl ester, at a temperature of 150–200° C.

In general, the carboxylic acid compounds that react with the tin transesterification catalyst to produce the insoluble derivatives include aliphatic, aromatic, heteroaromatic carboxylic acids of the mono-, di-, tri- and polycarboxylic acid type. Hydrates of these acids are also useful. Preferred carboxylic acids are those of the di-, tri- and polycarboxylic acid type (for example, ethylenediaminetetraacetic acid (EDTA)); and more preferably, are those of the dicarboxylic acid type such as oxalic acid, citric aid, maleic acid, malic acid, ascorbic acid, adipic acid and the like, and hydrates thereof. Most preferably, the carboxylic acid is oxalic acid dihydrate. Hereinafter, the reaction between the tin compound and the carboxylic acid compound will be termed the "tin removal" reaction.

In general, about 20 moles to about 1 mole of carboxylic acid are used for each mole of tin compound. Preferably, about 10 moles to about 1 mole of carboxylic acid are used for each mole of tin compound. Most preferably, about 5 moles to about 1 mole of carboxylic acid are used for each mole of tin compound.

The tin removal reaction may take place at atmospheric pressure or under reduced pressure. Preferably, the reaction proceeds at a reduced pressure of between about 250 to about 1 mm of Hg, more preferably, at a reduced pressure of between about 50 to about 1 mm Hg. Most preferably, the reaction proceeds at a reduced pressure of between about 10 to about 1 mm Hg.

In general, the tin removal reaction takes place at a temperature above the melting point, but below the decomposition temperature, of the carboxylic acid used. Preferably, the reaction takes place between at least about 100° C. and about 230° C., more preferably between about 110° C. and about 190° C., most preferably between about 110° C. and about 160° C.

The tin removal reaction proceeds until the tin transesterification catalyst forms an insoluble derivative. In general, the reaction proceeds at a temperature of about 110 to about 130° C. for at least about two hours, preferably about one hour. Most preferably, the reaction proceeds for at least about 0.5 hours.

Upon completion of the reaction, the reaction mass is filtered at a temperature of about 110 to about 130° C. under pressure using a filter of suitable porosity. A filter on the order of about 0.5 micron porosity has been found to be particularly effective. The filtration should take place at a temperature whereby the compound of formula (I) is rendered molten or at least with a viscosity low enough to be filterable so that the insoluble tin compound is easily separated therefrom.

It is important to note that that tin compounds are effective catalysts in reactions that produce various compounds other than those of the instant invention. Examples include, but are not limited to, transesterification reactions resulting in 3-(2H-benzotriazol-2-yl)-5-(1,1-dimethylethyl)-4-hydroxybenzenepropanoic acid, octyl esters and 3-(2H-benzotriazol-2-yl)-5-(1,1-dimethylethyl)4-hydroxybenzenepropanoic acid, poly(ethylenedioxy) esters; transesterification of acrylates; esterification resulting in the production of plasticizers like dioctyl phthalate, synthetic lubricants, and fatty acid esters; production of polyester resins; and epoxy acid reactions. It is herein contemplated that the instant tin removal reaction may be useful in removing tin from any reaction mass or product where residual tin may be undesirable.

The following experiments are illustrative of the process according to the invention and are not to be construed to limit the scope of the instant invention in any manner whatsoever.

EXAMPLES

Materials

Methyl 3,5-di-t-butyl-4-hydroxyhydrocinnamate, M.W. 292.4, 100% purity.

1-Octadecanol, M.W. 270.5, 98.5% purity, available from Procter & Gamble.

Isooctanol ($C_7$–$C_9$ alcohols), M.W. 130.2, 99.0% purity (wt % alcohol), available from Exxon Chemical under the trademark EXXAL® 8.

Monobutyltin tris(2-ethylhexoate), M.W. 605.4, >98% purity, available from Elf Atochem under the trademark FASCAT® 9102/4102.

FASCAT® 4215A organotin catalyst, an organotin catalyst of proprietary structure belonging to the stannoxane family and containing 18.5–20.5% tin. Available in an aromatic hydrocarbon solution designed for transesterification reactions from Elf Atochem.

Stannous bis(2-ethylhexoate), M.W. 404.9, 75–90% purity, available from Elf Atochem under the trademark FASCAT® 2003.

Oxalic acid dihydrate, M.W. 126.07, 99.8% purity, available from Mallinckrodt.

Equipment

Size 1.5 liter double jacketed reactor equipped with a heating/cooling bath using silicone fluid as the heat transfer media, mechanical stirrer, thermocouple, nitrogen inlet, and a heated overhead condenser connected in series to a dry ice/2-propanol trap and a vacuum pump.

Size 800 ml stainless steel pressure filter, model 60201-800 available from Creative Scientific Equipment Corp., used with ASBESTOCEL® filter pads, model number 100AC060050 also available from Creative Scientific Equipment Corp., and electrical heating tape.

Definitions

Unless otherwise specified, all temperatures are set forth in degrees Celsius and all parts and percentages are by weight.

Procedure

Example 1

Preparation and Purification of Octadecyl 3.5-Di-t-butyl-4-hydroyydrocinnamate Under Reduced Pressure The reactor is charged with 307.0 grams (1.05 moles) methyl 3,5-di-t-butyl-4-hydroxyhydrocinnamate and 270.5 grams (1.00 mole) 1-ocadecanol, and the reaction mass is heated to 100° C. under nitrogen flow. After the reactants are molten, agitation is set. The reaction mass is held at 100° C., and a vacuum of 5 mm Hg is pulled, held for 30 minutes and then broken.

The reaction mass is heated to 170° C. under nitrogen flow and then charged with the tin catalyst (see Table I below for the exact nature of the tin catalyst). The vacuum is slowly lowered to 2–3 mm Hg over 3 minutes. The reaction mass is then held at 170° C. and 2 mm Hg for one hour. The vacuum is broken, and the reaction mass is cooled to 110° C. Table I shows the components of the crude reaction mass, as measured by gas chromatography.

Oxalic acid dihydrate (0.18% by weight of the total reaction mass) is then charged into the reaction mass, and the vacuum is immediately pulled to 2–3 mm Hg. The system is held at 110° C. and 2 mm Hg for 30 minutes, after which time the vacuum is broken, and the reaction mass is filtered through a pressure filter with a 5 micron filter pad. Table I shows the components of the purified reaction mass, as measured by gas chromatography.

The amount of tin catalyst removed is presented in Table I below.

TABLE I

Purification of Octadecyl 3,5-Di-t-butyl-4-Hydroxyhydrocinnamate Under Reduced Pressure

| Sample | Tin Catalyst | Ppm Sn in Reaction (calculated) | Ppm Sn in Crude Reaction Mass | Ppm Sn in Filtrate | % Removal of Sn |
|---|---|---|---|---|---|
| 1 | dioctyltin oxide | 100 | 100 | 7 | 93% |
| 2 | FASCAT® 4215A | 200 | 169 | 11 | 93% |
| 3 | FASCAT® 4102 | 200 | 192 | 4 | 98% |
| 4 | FASCAT® 4102 | 100 | 113 | 0 | 100% |
| 5 | FASCAT® 4102 | 60 | 65 | 0 | 100% |
| 6 | FASCAT® 4102 | 25 | 26 | 0 | 100% |
| 7 | FASCAT® 2003 | 200 | 200 | 2 | 99% |

Example 2

Preparation and Purification of Octadecyl 3.5-Di-t-butyl-4-hydroxyhydrocinnamate Under Atmospheric Pressure The procedure according to Example 1 was followed except that the tin removal step was conducted at atmospheric pressure. Results are presented in Table II below.

TABLE II

Purification of Octadecyl 3,5-Di-t-butyl-4-hydroxyhydrocinnamate Under Atmospheric Pressure

| Tin Catalyst | ppm Sn in Reaction (calculated) | ppm Sn in Crude Reaction Mass | ppm Sn in Filtrate | % Removal of Sn |
|---|---|---|---|---|
| FASCAT® 4215A | 200 | 192 | 4 | 97.9% |

Example 3

Preparation and Purification of Isooctyl 3.5-Di-t-butyl-4-hydroxyhydrocinnamate

The reactor is charged with 350.9 g (1.20 moles) of methyl 3,5-di-t-butyl4-hydroxyhydrocinnamate and 179.4 g (1.38 moles) of isooctanol ($C_7$–$C_9$ alcohols), and heated to 90° C. under nitrogen. After the reactants are molten, agitation is set at 300 rpm. The reaction mass is held at 90° C., and the vacuum is lowered to 10 mm Hg for 30 minutes and then broken.

FASCAT® 4215A (0.2 g) is charged to the reaction mass. The reactor atmosphere is rendered inert by twice pulling vacuum to 50 mm Hg and breaking the vacuum with nitrogen. The vacuum is then immediately pulled to 75 mm Hg, and the reaction mass heated to 120° C. The temperature is then slowly increased to 160° C., at which temperature the reaction mass is held for 3 hours. The vacuum is then lowered to remove the excess isooctanol by distillation. The vacuum is broken, and the reaction mass cooled to 100° C. Table III shows the components of the crude reaction mass, as measured by gas chromatography.

Oxalic acid dihydrate (0.20% by weight of the total reaction mass) is charged into the reaction mass, and vacuum is lowered to 2 mm Hg. After 30 minutes, the vacuum is broken, and the reaction mass is filtered through a pressure filter with a 5 micron filter pad. Table III shows the components of the purified reaction mass, as measured by gas chromatography.

TABLE III

Purification of Isooctyl 3,5-Di-t-butyl-4-hydroxyhydrocinnamate

| Tin Catalyst | ppm Sn in reaction (calculated) | ppm Sn in Crude Reaction Mass | ppm Sn in Filtrate | % Removal of Sn |
|---|---|---|---|---|
| FASCAT® 4215A | 100 | 96 | 1 | 99.0% |

Examples 4–5

Preparation and Purification of Other Substituted HydroxE phenylcarboxylic Acid Esters Using the general procedure of any of Examples 1–3 with either a methyl or ethyl ester of a substituted hydroxyhydrocinnamic acid, various alkanols and any of the tin transesterification catalysts described herein, the following higher esters of formula (I) are obtained in high yield and purity. The tin transesterification catalyst is removed from the tin catalyzed transesterification reaction mass by reacting the transesterification reaction mass with a carboxylic acid until the tin catalyst forms an insoluble derivative, and then separating the insoluble derivative from the reaction mass by filtration. Efficiency of tin removal is similar to the above Examples 1–3.

| Example | R | A |
|---------|---|---|
| 4 | tert-butyl | lauryl |
| 5 | tert-butyl | n-octyl |

Examples 6–13

Preparation and Purification of Other Substituted Hydroxyphenylcarboxylic Acid Esters Using the general procedure of any of Examples 1–3 with either the methyl or ethyl ester of a substituted hydroxyhydrocinnamic acid, various polyols and any of the tin transesterification catalysts described herein, the following higher esters of formula (I) are obtained in high yield and purity. The tin transesterification catalyst is removed from the tin catalyzed transesterification reaction mass by reacting the transesterification reaction mass with a carboxylic acid until the tin catalyst forms an insoluble derivative, and then separating the insoluble derivative from the reaction mass by filtration. Efficiency of tin removal is similar to the above Examples 1–3.

| Example | n | R | A |
|---------|---|---|---|
| 6 | 2 | tert-butyl | hexamethylene |
| 7 | 2 | methyl | —CH$_2$CH$_2$SCH$_2$CH$_2$— |
| 8 | 2 | tert-butyl | —CH$_2$CH$_2$SCH$_2$CH$_2$— |
| 9 | 2 | tert-butyl | —CH$_2$CH$_2$(OCH$_2$CH$_2$)$_2$— |
| 10 | 3 | tert-butyl | CH$_3$C(CH$_2$—)$_3$ |
| 11 | 3 | tert-butyl | CH$_3$C(CH$_2$—)$_3$ |
| 12 | 4 | tert-butyl | pentaerythrityl |
| 13 | 4 | methyl | pentaerythrityl |

What is claim is:

1. An improved process for the preparation of a compound of formula (I)

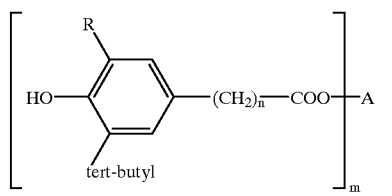

(I)

wherein R is an alkyl of 1 to 4 carbon atoms, n is 0 to 2, m is 1 to 4; and when m is 1, A is a straight or branched chain alkyl of 4 to 18 carbon atoms;

when m is 2, A is a straight or branched chain alkylene of 2 to 12 carbon atoms, or said alkylene interrupted by one to five O or S atoms, or A is 2,2-bis(4-ethyleneoxyphenyl) propane;

when m is 3, A is a straight or branched chain alkanetriyl of 3 to 6 carbon atoms; and when m is 4, A is pentaerthrityl, by transesterifying the corresponding lower alkyl ester with an alcohol of the formula (II)

$$A\text{-}(OH)_m \quad (II)$$

in the presence of a tin catalyst;

wherein the improvement comprises reacting the tin catalyzed transesterification reaction mass with a carboxylic acid or hydrate thereof neat, in the absence of an aqueous medium, until the tin catalyst forms an insoluble derivative, and separating the insoluble derivative from the reaction mass by filtration.

2. A process according to claim 1 where the lower alkyl ester is methyl or ethyl 3,5-di-tert-butyl4-hydroxyhydrocinnamate.

3. A process according to claim 2 where the lower alkyl ester is methyl 3,5-di-tert-butyl4-hydroxyhydrocinnamate.

4. A process according to claim 1 where, in the compounds of formula (I), R is methyl or tert-butyl.

5. A process according to claim 1 where, in the compound of formula (I), m is 1, and A is alkyl of 8 to 18 carbon atoms.

6. A process according to claim 5 wherein A is isooctyl, lauryl or n-octadecyl.

7. A process according to claim 6 wherein A is n-octadecyl.

8. A process according to claim 1 where, in the compound of formula (I), m is 2 and A is hexamethylene, —CH$_2$CH$_2$SCH$_2$CH$_2$— or —CH$_2$CH$_2$OCH$_2$CH$_2$OCH$_2$CH$_2$—.

9. A process according to claim 1 where, in the compound of formula (I), m is 3 and A is CH$_3$C(CH$_2$—)$_3$, CH$_3$CH$_2$C(CH$_2$—)$_3$, or glyceryl.

10. A process according to claim 1 wherein the compound of formula (I) is isooctyl 3,5-di-tert-butyl4-hydroxyhydrocinnamate, n-octadecyl 3,5-di-tert-butyl4-hydroxyhydrocinnamate, or pentaerythrityl tetrakis (3,5-di-tert-butyl4-hydroxyhydrocinnamate).

11. A process according to claim 1 where the reaction between the tin catalyzed transesterification reaction mass and the carboxylic acid takes place under reduced pressure.

12. A process according to claim 1 wherein the carboxylic acid is of the di-, tri- or polycarboxylic acid type.

13. A process according to claim 1 wherein the carboxylic acid is of the dicarboxylic acid type.

14. A process according to claim 1 wherein the carboxylic acid is oxalic acid, citric acid, maleic acid, malic acid, ascorbic acid, adipic acid, ethylenediaminetetraacetic acid (EDTA), or a hydrate thereof.

15. A process according to claim 1 where the carboxylic acid is oxalic acid dihydrate.

16. A process according to claim 1 where the reaction temperature is equal to or greater than the melting point of the carboxylic acid.

17. A process according to claim 1 where the carboxylic acid is present in a ratio of about 5 moles to about 1 mole of tin catalyst.

18. A process according to claim 1 wherein the tin catalyst is a monoalkyltin ester, dialkyltin ester, monoalkyltin oxide, dialkyltin oxide, tin tetrachloride, monoalkyltin trichloride, dialkyltin dichloride, diaryltin dichloride, organotin sulfide, organotin sulfate, organotin mercaptan, organotin carboxylic acid or ester thereof, or a stannoxane.

19. A process according to claim 1 wherein the tin catalyst is a monoalkyltin ester, dialkyltin ester, monoalkyltin oxide, dialkyltin oxide, tin tetrachloride, monoalkyltin trichloride, dialkyltin dichloride, diaryltin dichloride, organotin carboxylic acid or ester thereof, or a stannoxane.

20. A process according to claim 19 wherein the tin catalyst is monobutyltin tris(2-ethylhexoate), dibutyltin bis(2ethylhexoate), stannous bis(2-ethylhexoate), dibutyltin diacetate, dibutyltin oxide, butyltin trichloride, butyltin trimethylate, dibutyltin dichloride or diphenyltin dichloride.

21. A process according to claim 20 wherein the catalyst is monobutyltin tris(2-ethylhexoate).

22. A process according to claim 20 wherein the tin catalyst is stannous bis(2-ethylhexoate).

* * * * *